(12) United States Patent
Watanabe et al.

(10) Patent No.: US 11,071,511 B2
(45) Date of Patent: Jul. 27, 2021

(54) RADIATION TOMOGRAPHIC IMAGING SYSTEM AND PROGRAM FOR CONTROLLING THE SAME

(71) Applicant: General Electric Company, Schenectady, NY (US)

(72) Inventors: Motoki Watanabe, Hino (JP); Yotaro Ishihara, Hino (JP)

(73) Assignee: General Electric Company, Schenectady, NY (US)

( * ) Notice: Subject to any disclaimer, the term of this patent is extended or adjusted under 35 U.S.C. 154(b) by 158 days.

(21) Appl. No.: 16/077,536

(22) PCT Filed: Feb. 16, 2017

(86) PCT No.: PCT/US2017/018121
§ 371 (c)(1),
(2) Date: Aug. 13, 2018

(87) PCT Pub. No.: WO2017/146985
PCT Pub. Date: Aug. 31, 2017

(65) Prior Publication Data
US 2019/0059843 A1    Feb. 28, 2019

(30) Foreign Application Priority Data

Feb. 22, 2016   (JP) .............................. JP2016-030889

(51) Int. Cl.
*A61B 6/00* (2006.01)
*A61B 6/03* (2006.01)
(Continued)

(52) U.S. Cl.
CPC .............. *A61B 6/544* (2013.01); *A61B 6/032* (2013.01); *A61B 6/488* (2013.01); *H05G 1/26* (2013.01); *A61B 6/0407* (2013.01)

(58) Field of Classification Search
CPC .. A61B 6/544; A61B 6/00; A61B 6/54; A61B 6/52; A61B 6/40; A61B 6/42; A61B 6/08; A61B 6/02
See application file for complete search history.

(56) References Cited

U.S. PATENT DOCUMENTS 4,047,036 A * 9/1977 Smith .................. G01B 15/045
378/56
5,379,333 A * 1/1995 Toth ....................... A61B 6/032
378/108
(Continued)

OTHER PUBLICATIONS

International Search Report and Written Opinion for the following corresponding PCT application PCT/US2017/018121 dated May 9, 2017; having a total of 12 pages.

*Primary Examiner* — David P Porta
*Assistant Examiner* — Djura Malevic (57) ABSTRACT

An X-ray CT system comprises: a storage device for storing therein a referential emission condition defined assuming at least one of a required referential width and a required referential body depth in a subject and defined taking account of a degree of X-ray absorption in the subject; a camera and a distance sensor for detecting a width and a body depth of the subject; and an emission condition setting section 76 for setting an emission condition for X-rays emitted by an X-ray tube in imaging after correcting the referential emission condition according to at least one of a difference between the detected width of the subject and the referential width and a difference between the body depth of the subject detected by the optical sensor and the referential body depth.

11 Claims, 9 Drawing Sheets

(51) Int. Cl.
 *H05G 1/26* (2006.01)
 *A61B 6/04* (2006.01)

(56) References Cited

U.S. PATENT DOCUMENTS

| | | | | |
|---|---|---|---|---|
| 5,386,446 A | * | 1/1995 | Fujimoto | A61B 6/06 378/20 |
| 5,692,507 A | * | 12/1997 | Seppi | A61B 6/032 128/920 |
| 5,822,393 A | * | 10/1998 | Popescu | A61B 6/032 378/108 |
| 6,385,280 B1 | * | 5/2002 | Bittl | A61B 6/032 378/106 |
| 8,300,764 B2 | * | 10/2012 | Yamaguchi | G06T 7/73 378/62 |
| 8,908,832 B2 | * | 12/2014 | Yamashita | A61B 6/06 378/62 |
| 10,004,465 B2 | * | 6/2018 | Krauss | A61B 6/032 |
| 10,430,551 B2 | * | 10/2019 | Wang | G16H 30/20 |
| 10,470,738 B2 | * | 11/2019 | Feuerlein | A61B 6/5205 |
| 10,531,850 B2 | * | 1/2020 | Tkaczyk | A61B 6/0487 |
| 2002/0080910 A1 | * | 6/2002 | Kuroda | A61B 6/4085 378/19 |
| 2003/0016778 A1 | * | 1/2003 | Tachizaki | A61B 6/583 378/4 |
| 2003/0099323 A1 | * | 5/2003 | Nagata | A61B 6/585 378/4 |
| 2003/0123603 A1 | * | 7/2003 | Suzuki | A61B 6/027 378/4 |
| 2006/0182322 A1 | * | 8/2006 | Bernhardt | A61B 5/02007 382/128 |
| 2006/0231590 A1 | * | 10/2006 | Hirano | H01J 37/301 228/101 |
| 2009/0154647 A1 | * | 6/2009 | Matsuzawa | A61B 6/04 378/98 |
| 2014/0355735 A1 | * | 12/2014 | Choi | A61B 6/544 378/8 |
| 2015/0104092 A1 | * | 4/2015 | Flohr | G06K 9/4604 382/131 |
| 2015/0327821 A1 | * | 11/2015 | Hu | A61B 6/5205 378/62 |
| 2015/0327830 A1 | | 11/2015 | Hu | |
| 2017/0007196 A1 | * | 1/2017 | Don | G01B 11/06 |
| 2019/0035118 A1 | * | 1/2019 | Zhao | G06T 5/002 |

\* cited by examiner

| Body part | Width & Body depth | Referential tube current |
|---|---|---|
| Head | Wb1·Db1 | mAb1 |
| Neck | Wb2·Db2 | mAb2 |
| Shoulders | Wb3·Db3 | mAb3 |
| Lungs | Wb4·Db4 | mAb4 |
| Abdomen | Wb5·Db5 | mAb5 |
| Hips | Wb6·Db6 | mAb6 |
| Lower limbs | Wb7·Db7 | mAb7 |

RADIATION TOMOGRAPHIC IMAGING SYSTEM AND PROGRAM FOR CONTROLLING THE SAME

This application is a filing under 35 U.S.C. 371 of international application number PCT/US2017/018121, filed Feb. 16, 2017, which claims priority to Japan application number 2016-030889, filed Feb. 22, 2016, the entire disclosure of each of which is hereby incorporated by reference.

FIELD OF THE INVENTION

The present invention relates to a radiation tomographic imaging system and a program for controlling the same, for setting conditions for radiation emission to a subject based on at least one of the subject's width and body depth.

BACKGROUND

Functions provided in a radiation tomographic imaging apparatus include an automatic exposure control mechanism. The automatic exposure control mechanism automatically controls the output power of radiation emitted to a subject based on data indicating a distribution of a radiation absorbed dose in the subject acquired beforehand so that the power is increased for a position at which the radiation absorbed dose is greater and is decreased for a position at which the radiation absorbed dose is smaller.

The automatic exposure control mechanism will now be further described. First, a preliminary scan in which a low dose of radiation is emitted onto a subject, i.e., a scout scan, is performed. Then, from projection data obtained in the scout scan are determined an area of a profile of the projection data, an ellipticity obtained by elliptically approximating a cross section across the body axis of the subject, a radiation decrement, etc. for each position in a direction of the body axis of the subject. The output power of emitted radiation, for example, the tube current value for a radiation tube, is then set for each position in the body-axis direction of the subject based on information on the area, ellipticity, decrement, etc. so that the amount of noise is uniform over a reconstructed image (see Patent Document 1). A main scan is then performed with the set output power.

PRIOR ART REFERENCE

[Patent Document 1] Japanese Patent Application KOKAI No. 2001-043993

SUMMARY OF THE INVENTION

However, because of the need for performing the scout scan separately from the main scan as described above, a more improved throughput is desired. In particular, the scout scan is performed twice: one from just above the subject, and the other from just the side of the subject. Specifically, a first scout scan is performed by moving a table carrying thereon the subject while emitting radiation from the radiation tube lying at a 0-degree position, and then, the table is brought back to its original position, whereafter a second scout scan is performed by moving the table carrying thereon the subject again while emitting radiation from the radiation tube lying at a 90-degree position. Therefore, a more improved throughput is desired.

Moreover, the radiation exposure dose for the subject increases corresponding to the fact that the scout scan should be performed. From such circumstances, it is desired to set conditions for radiation emission in the automatic exposure control mechanism without performing a scout scan. Nevertheless, it is also desired to set suitable conditions for radiation emission without performing a scout scan to a degree of suitability comparable to a degree that would be otherwise achieved when the scout scan is performed, that is, to set conditions for radiation emission with which the amount of noise in a reconstructed image fulfills a required amount of noise.

The invention made for solving the aforementioned problems is a radiation tomographic imaging system characterized in comprising: a radiation tube for emitting radiation onto a subject; a storage device for storing therein a referential emission condition for radiation emitted by said radiation tube, said referential emission condition being defined assuming at least one of a required referential width and a required referential body depth in said subject and defined taking account of a degree of absorption of said radiation in said subject; an optical sensor for detecting at least one of a width and a body depth of said subject; and an emission condition setting section for setting an emission condition for radiation emitted by said radiation tube in imaging after correcting said referential emission condition according to at least one of a difference between the width of said subject detected by said optical sensor and said referential width, and a difference between the body depth of said subject detected by said optical sensor and said referential body depth.

According to the invention in the aspect described above, the referential emission condition is corrected according to at least one of a difference between the subject's width detected by the optical sensor and the referential width and a difference between the subject's body depth detected by the optical sensor and the referential body depth to set a condition for radiation emission in imaging. The referential emission condition is defined taking account of a degree of absorption of radiation reflecting factors like the subject's width and body depth, and in addition, other factors. Since such a referential emission condition is corrected according to at least one of a difference between the subject's width detected by the optical sensor and the referential width and a difference between the subject's body depth detected by the optical sensor and the referential body depth, it is possible to set a suitable condition for radiation emission without performing a scout scan to a degree of suitability comparable to a degree that would be otherwise achieved when the scout scan is performed.

Figure 1:
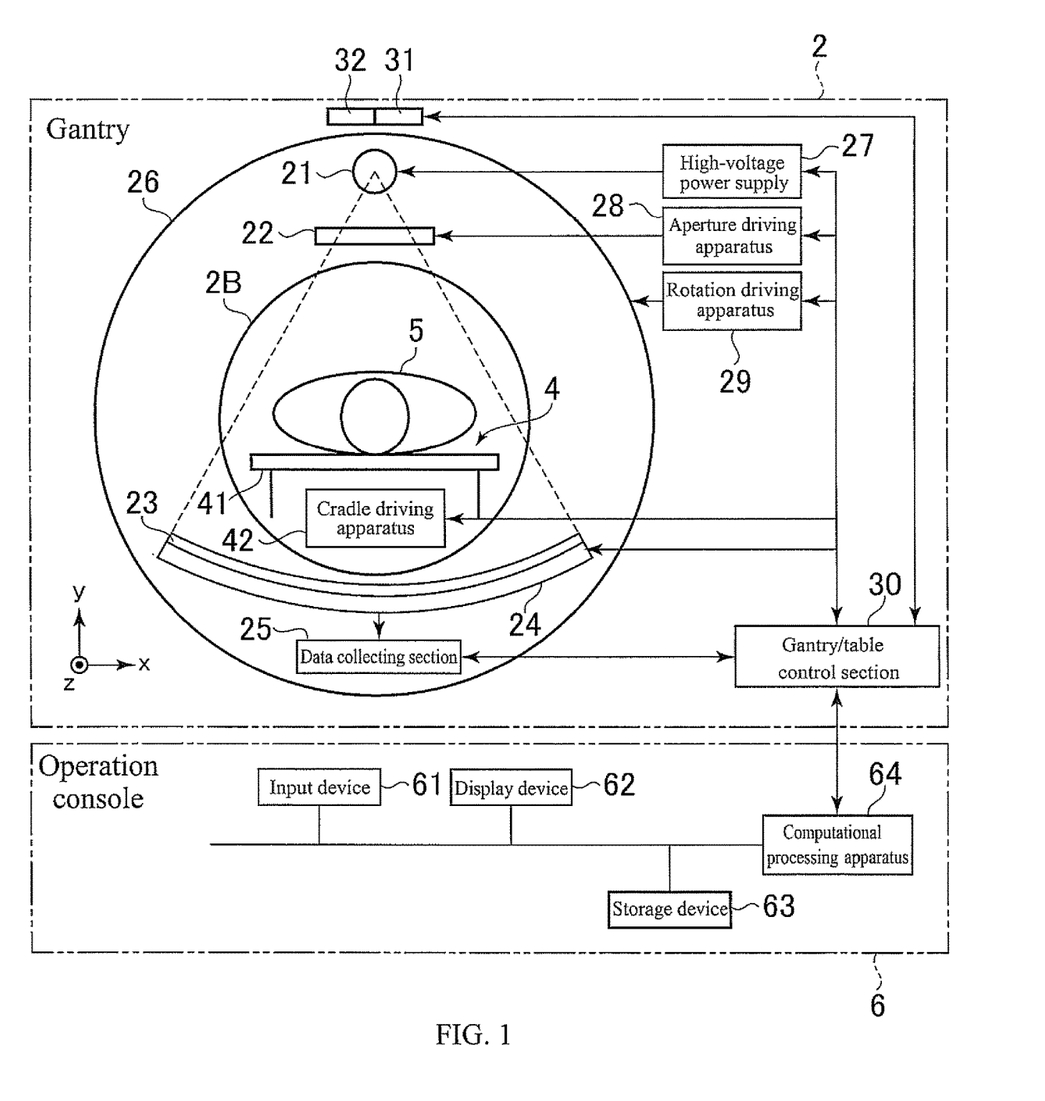
FIG. 1 A diagram schematically showing a hardware configuration of an X-ray CT system in accordance with embodiments.

To begin with, a first embodiment will be described. FIG. 1 shows an X-ray CT system 1, which is an exemplary embodiment of the radiation tomographic imaging system in the present invention. As shown in FIG. 1, the X-ray CT system 1 comprises a gantry 2, an imaging table 4, and an operation console 6.

Figure 2:
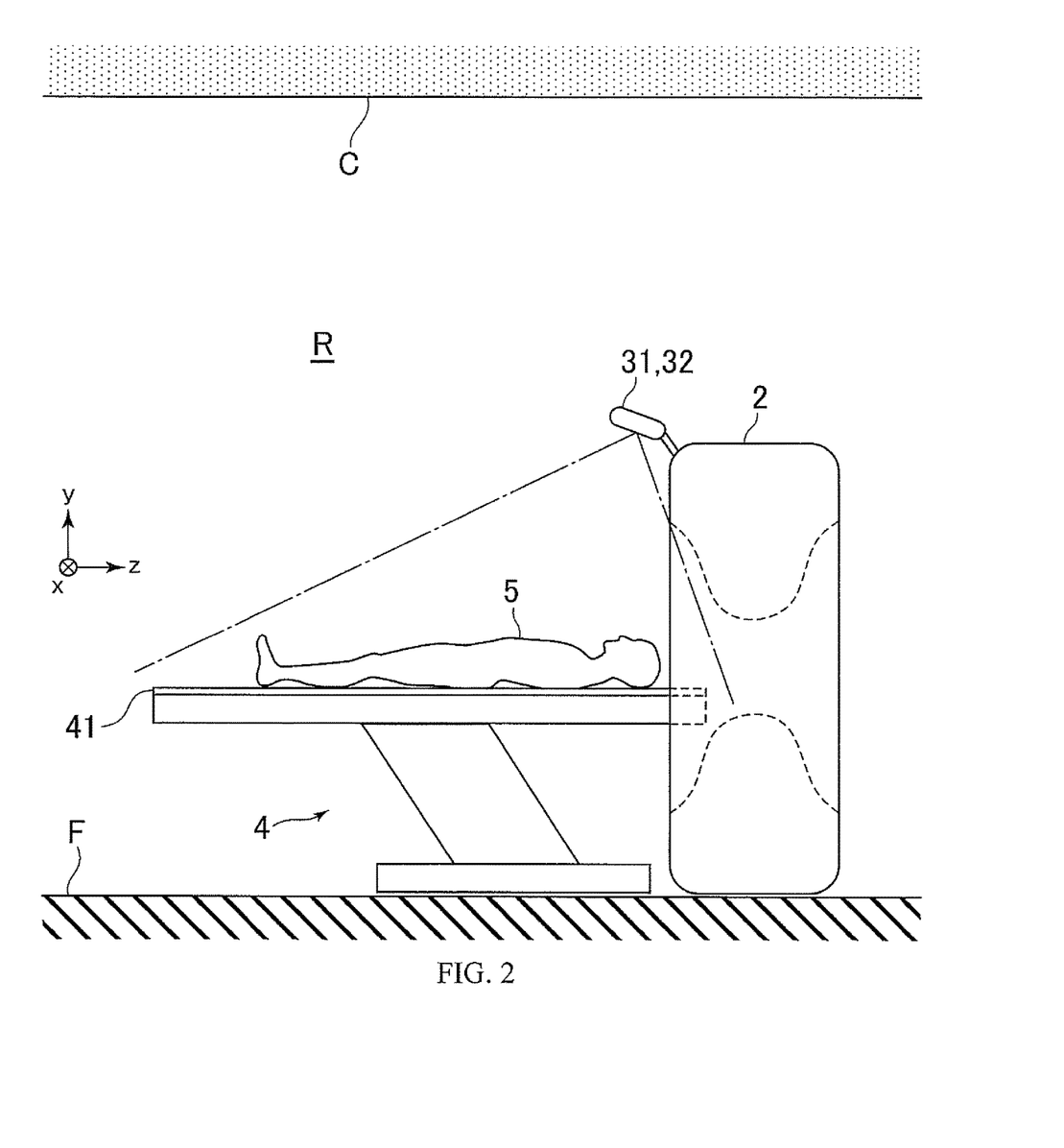
FIG. 2 A view showing an exemplary overview of an imaging room.

The gantry 2 and imaging table 4 are installed in an imaging room R, as shown in FIG. 2. The console 6 is installed in an operation room (not shown) different from the imaging room R.

In FIG. 2, reference symbol F designates a floor of the imaging room R, and reference symbol C designates a ceiling of the imaging room R.

Referring back to FIG. 1, the gantry 2 has an X-ray tube 21, an aperture 22, a collimator device 23, an X-ray detector 24, a data collecting section 25, a rotating section 26, a high-voltage power source 27, an aperture driving apparatus 28, a rotation driving apparatus 29, and a gantry/table control section 30, a camera 31 and a distance sensor 32.

The rotating section 26 is rotatably supported around a bore 2B of the gantry 2. The rotating section 26 has the X-ray tube 21, aperture 22, collimator device 23, X-ray detector 24, and data collecting section 25 mounted thereon.

The X-ray tube 21 and X-ray detector 24 are disposed to face each other across the bore 2B. The X-ray tube 21 is an exemplary embodiment of the radiation tube in the present invention.

The aperture 22 is disposed between the X-ray tube 21 and bore 2B. It shapes X-rays emitted from an X-ray focus of the X-ray tube 21 toward the X-ray detector 24 into a fan beam or a cone beam.

The collimator device 23 is disposed between the bore 2B and X-ray detector 24. The collimator device 23 removes scatter rays that would otherwise impinge upon the X-ray detector 24.

The X-ray detector 24 has a plurality of X-ray detector elements two-dimensionally arranged in a direction (referred to as channel direction) of the span of the fan-shaped X-ray beam emitted from the X-ray tube 21 and a direction (referred to as row direction) of the thickness thereof. Each respective X-ray detector element detects X-rays passing through a subject 5 laid in the bore 2B, and outputs an electric signal depending upon the intensity of the X-rays.

The data collecting section 25 receives the electric signal output from each X-ray detector element in the X-ray detector 24, and converts it into X-ray data for collection.

The imaging table 4 has a cradle 41 and a cradle driving apparatus 42. The subject 5 is laid on the cradle 41. The cradle driving apparatus 42 moves the cradle 41 into/out of the bore 2B, i.e., an imaging volume, in the gantry 2.

The high-voltage power source 27 supplies high voltage and current to the X-ray tube 21.

The aperture driving apparatus 28 drives the aperture 22 and modifies the shape of its opening.

The rotation driving apparatus 29 rotationally drives the rotating section 26.

The gantry/table control section 30 controls several apparatuses and sections in the gantry 2, the imaging table 4, and the like.

The camera 31 and distance sensor 32 are attached to the gantry 20 on its upper portion. The camera 31 is an optical imaging apparatus for detecting visible light and acquires an image of the subject 5 laid on the cradle 41 of the imaging table 4. The distance sensor 32 has an emitting section (not shown) for emitting, for example, infrared rays, and a detecting section (not shown) for detecting the infrared rays emitted from the emitting section and reflected back. By the distance sensor 32, a distance between the distance sensor 32 and an infrared reflector is detected. It should be noted that image signals from the camera 31 and detection signals from the distance sensor 32 are passed through the gantry/table control section 30 and input into a computational processing apparatus 64 in the operation console 6.

According to the image acquired by the camera 31, a width of the subject 5 may be detected. According to the detection signals from the distance sensor 32, a body depth of the subject 5 may be detected. Details thereof will be discussed later. The camera 31 and distance sensor 32 constitute an exemplary embodiment of the optical sensor in the present invention.

The operation console 6 accepts several kinds of operation from an operator. The operation console 6 has an input device 61, a display device 62, a storage device 63, and the computational processing apparatus 64. In the present embodiment, the operation console 6 is constructed from a computer.

The input device 61 is configured to include a button, a keyboard, etc. for accepting an input of a command and information from the operator, and to further include a pointing device, and the like. The display device 62 is an LCD (Liquid Crystal Display), an organic EL (Electro-Luminescence) display, or the like. The display device 62 is an exemplary embodiment of the display device in the present invention.

The storage device 63 is an HDD (Hard Disk Drive), semiconductor memory, such as RAM (Random Access Memory) and ROM (Read Only Memory), and the like. The operation console 6 may have all of the HDD, RAM, and ROM as the storage device 63. The storage device 63 may also comprise a portable storage medium, such as a CD (Compact Disk) or a DVD (Digital Versatile Disk). The storage device 63 is an exemplary embodiment of the storage device in the present invention.

The computational processing apparatus 64 is a processor such as a CPU (central processing unit).

As shown in FIG. 1, a direction of the body axis of the subject 5, i.e., a direction of transportation of the subject 5 by the imaging table 4, will be referred to herein as z-direction. Moreover, a vertical direction will be referred to as y-direction, and a horizontal direction orthogonal to the y- and z-directions as x-direction.

Figure 3:
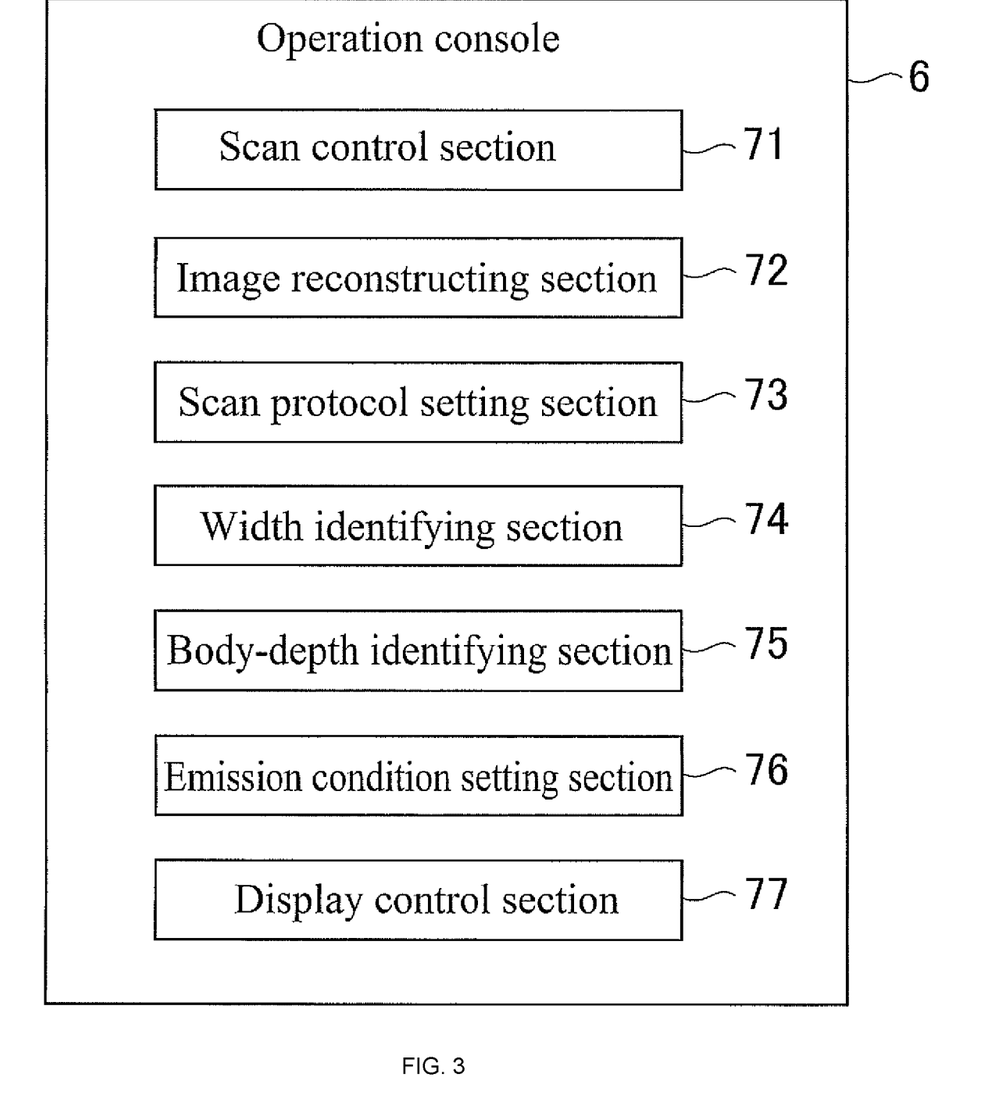
FIG. 3 A functional block diagram of an operation console in the X-ray CT system shown in FIG. 1.

Referring to FIG. 3, the operation console 6 has, as its function blocks, a scan control section 71, an image reconstructing section 72, a scan protocol setting section 73, a width identifying section 74, a body-depth identifying section 75, an emission condition setting section 76, and a display control section 77. The computational processing apparatus 64 executes functions of these scan control section 71, image reconstructing section 72, scan protocol setting section 73, width identifying section 74, body-depth identifying section 75, emission condition setting section 76, and display control section 77 by prespecified programs. The prespecified programs are stored in, for example, a non-transitory storage medium, such as the HDD or ROM, constituting the storage device 63. The programs may also be stored in a non-transitory storage medium having portability, such as the CD or DVD, constituting the storage device 63.

The scan control section 71 controls the gantry/table control section 30 in response to an operation by the operator to perform a scan.

The image reconstructing section 72 executes image reconstruction processing based on projection data obtained by scanning the subject 5 with X-rays emitted from the X-ray tube 21 to provide tomographic image data.

The scan protocol setting section 73 sets a scan protocol for use in performing the scan.

The width identifying section 74 identifies a width W of the subject 5 based on an image acquired by the camera 31. The width W is the dimension of the subject 5 in the x-axis direction. The width W may be identified at a plurality of positions in the body-axis direction.

The body-depth identifying section 75 identifies a body depth D of the subject 5 based on a detection signal from the distance sensor 32. The body depth D is the dimension of the subject 5 in the y-axis direction. The body depth D is identified in a portion for which the width W is identified. The body depth D may be identified at a plurality of positions in the body-axis direction.

The emission condition setting section 76 sets emission conditions for X-rays emitted by the X-ray tube 21 in imaging. For example, the emission condition setting section 76 sets a tube current in imaging (during a scan). Details thereof will be discussed later. The emission condition setting section 76 is an exemplary embodiment of the emission condition setting section in the present invention. The function by the emission condition setting section 76 is an exemplary embodiment of the emission condition setting function in the present invention.

The display control section 75 displays several kinds of images, including a tomographic image, and text on the display device 62.

Figure 4:
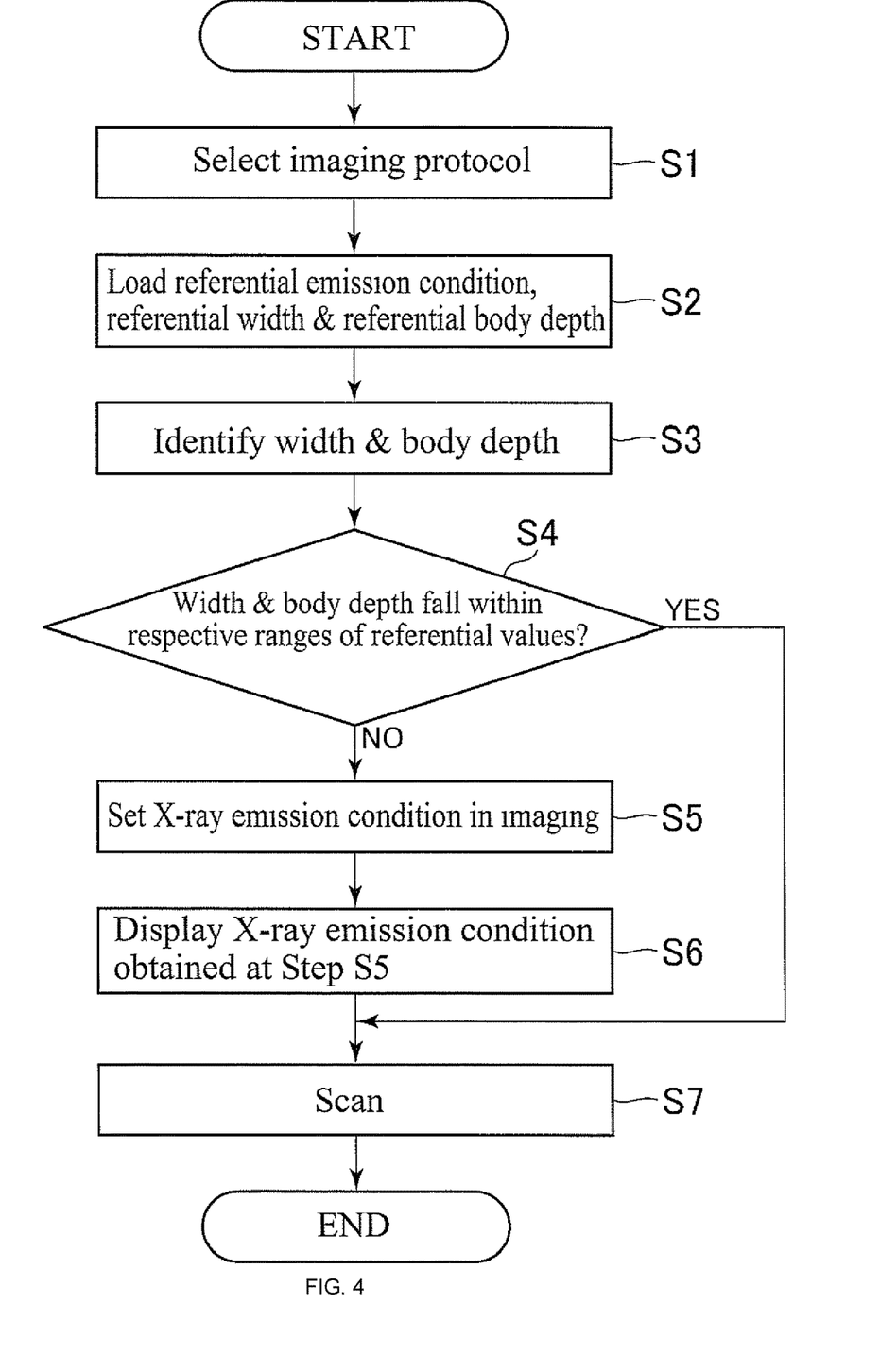
FIG. 4 A flow chart showing the flow of processing in the X-ray CT system in accordance with the embodiments.

Next, the flow of processing in the X-ray CT system in accordance with the present embodiment will be described based on the flow chart in FIG. 4. The description herein will address processing until a scan by X-rays is performed.

First, at Step S1, the operator selects an imaging protocol. The imaging protocol is input at the input device 61, for example.

Next, at Step S2, the emission condition setting section 76 loads thereon a referential emission condition, etc. This will be specifically described below. The referential emission condition is an emission condition when emitting X-rays by the X-ray tube 21 onto a subject of standard body shape. The referential emission condition is defined assuming a standard body shape, i.e., assuming a required referential width and a required referential body depth in the subject, and also defined taking account of the degree of X-ray absorption in the subject. The referential emission condition is an emission condition defined so that the noise level in a reconstructed image for a subject of standard body shape fulfills a level indicated by a required noise index value. The referential emission condition is stored in the storage device 63 for each body part in a subject. The referential emission condition is defined so that the noise level in a reconstructed image is uniform across body parts. In the present embodiment, the referential emission condition is a referential tube current.

The degree of X-ray absorption in a subject varies with the cross-sectional area of the subject determined by the width and body depth, and in addition, with what kind of substance, such as air or bone, is present in that body part. Accordingly, the referential tube current is set taking account of the degree of X-ray absorption in which the width and body depth, and in addition, other factors are reflected.

Figure 5:
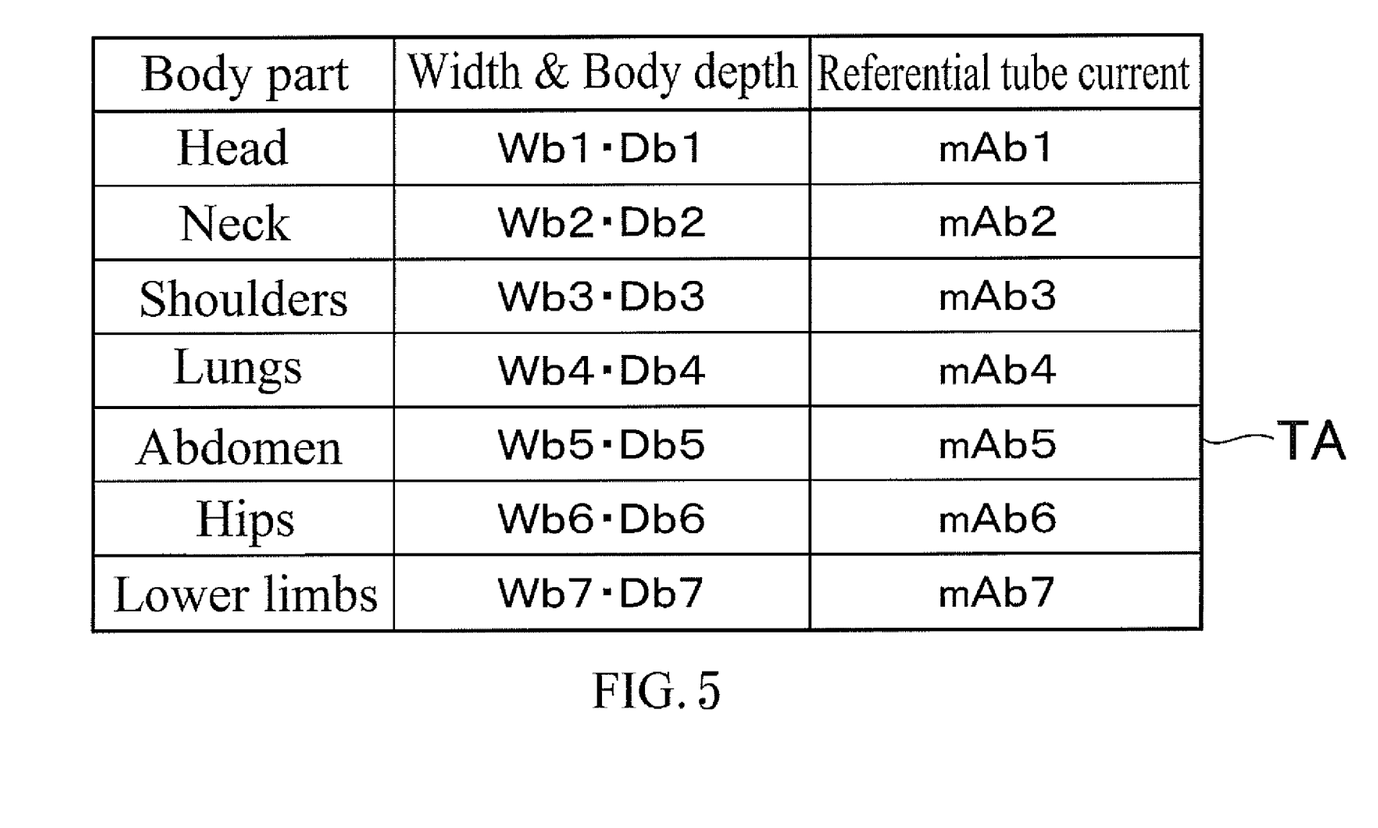
FIG. 5 A diagram showing a table stored in a storage device.

For example, the referential tube current is stored in the storage device 63 as Table TA shown in FIG. 5. Table TA is a table defining referential tube currents mAb1 to mAb7 depending upon the body part (a head, a neck, shoulders, lungs, an abdomen, hips, and lower limbs) of the subject. Some of the values mAb1 to mAb7 may be the same. As shown in FIG. 5, Table TA may include referential widths Wb1 to Wb7 and referential body depths Db1 to Db7. These referential widths Wb1 to Wb7 and referential body depths Db1 to Db7 constitute an exemplary embodiment of the required referential width and required referential body depth.

The emission condition setting section 76 loads from the storage device 63 information in Table TA for a body part according to the imaging protocol selected at Step S1. The information in Table TA loaded from the storage device 63 includes the referential tube current, referential width, and referential body depth for that body part. The body part may be a single part or comprises a plurality of parts.

Next, at Step S3, the width identifying section 74 identifies a width W of the subject 5. Moreover, the body-depth identifying section 75 identifies a body depth D of the subject 5. The width identifying section 74 and body-depth identifying section 75 identify the width W and body depth D for the body part according to the imaging protocol selected at Step S1.

The width identifying section 74 identifies the width W of the subject 5 based on an image acquired by the camera 31. The body-depth identifying section 75 identifies the body depth D by a difference between two distances: one being from the distance sensor 32 to the subject 5 at the body part, and the other being from the distance sensor 32 to a plane over which the subject 5 is laid on the imaging table 4.

Next, at Step S4, the emission condition setting section 76 decides whether the width W identified by the width identifying section 74 and body depth D identified by the body-depth identifying section 75 fall within respective ranges of the referential values. The range of the referential value is a range approved as representing the standard body shape, and is stored in the storage device 63. The range of the referential value approved as representing the standard body shape is such a range that the noise level in a reconstructed image fulfills a level indicated by a required noise index value when emitting X-rays with the referential tube current.

In the case that the width W and body depth D are decided not to fall within the respective ranges of the referential values at Step S4 ("NO" at Step S4), the flow goes to processing at Step S5. In the case that the width W and body depth D are decided to fall within the respective ranges of the referential values at Step S4 ("YES" at Step S4), the flow goes to processing at Step S7.

At Step S5, the emission condition setting section 76 corrects the referential emission condition to set a condition for emission of X-rays to the subject 5 in imaging. Here, the referential tube current loaded at Step S2 is corrected to set a tube current in imaging. The term imaging refers to a scan at Step S7, i.e., X-ray CT imaging, which will be discussed later.

Now correction of the referential tube current will be particularly described. The emission condition setting section 76 corrects the referential tube current according to two differences: one being between the width W of the subject 5 and referential width Wb, and the other being between the body depth D of the subject 5 and referential body depth Db. The difference may be a ratio or a (arithmetic) difference, for example. The referential width is one of the referential widths Wb1 to Wb7 in Table TA for the body part according to the imaging protocol. The referential body depth is one of the referential body depths Db1 to Db7 in Table TA for the body part according to the imaging protocol.

The emission condition setting section 76 corrects the referential tube current so that a higher tube current in imaging results as at least one of the width W and body depth D is larger, and a lower tube current in imaging results as at least one of the width W and body depth D is smaller. For example, the emission condition setting section 76 corrects the referential tube current mAb to calculate a tube current in imaging mA according to (EQ. 1) below:

$$mA=mAb*F \qquad (EQ. 1)$$

where $F=(W/Wb)*(D/Db)$.

According to (EQ. 1) above, a tube current mA with which the noise level in a reconstructed image fulfills a level indicated by a required noise index value is calculated.

In the case that the tube current mA is set for a plurality of body parts, the emission condition setting section 76 corrects the referential tube current mAb for each of the plurality of body parts according to (EQ. 1) for each of the plurality of body parts.

Figure 6:
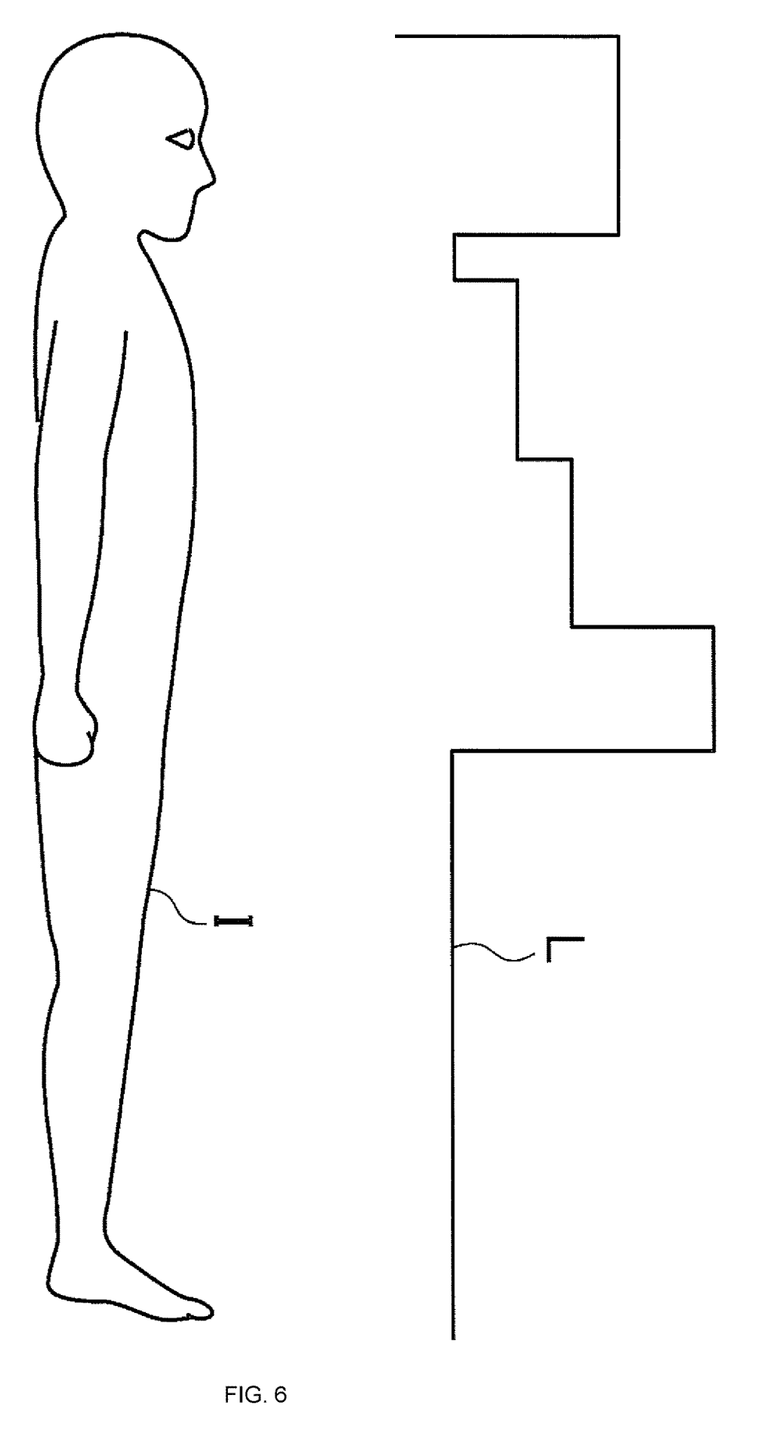
FIG. 6 A diagram showing a line chart representing a change of the tube current and a pictorial diagram representing a subject in a first embodiment.

Next, at Step S6, the display control section 77 displays on the display device 62 the X-ray emission condition, i.e., a tube current mA, set at Step S5. For example, the display control section 77 displays on the display device 62 a line chart L representing a change of the tube current mA in a direction of the body axis (z-axis direction) of the subject 5, as shown in FIG. 6. In FIG. 6, the horizontal direction represents the z-direction while the vertical direction represents the magnitude of the tube current mA. Here, the line chart L represents a change of the tube current mA in the whole body of the subject 5. The display control section 77 may display a pictorial diagram I representing the subject along with the line chart L on the display device 62. The line chart L is displayed so that the pictorial diagram I and the position in the z-axis direction correspond to each other.

In the case that the tube current in imaging mA is displayed at Step S6 and that the width W and body depth D are decided to fall within the respective ranges of the referential values at Step S4, the flow goes to processing at Step S7. At Step S7, a scan of the subject 5 with X-rays, i.e., X-ray CT imaging, is performed. The scan is performed by the scan control section 71 controlling the gantry/table control section 30. For example, in the case that the tube current mA is set at Step S5, a scan is performed with the tube current mA. On the other hand, in the case that the width W and body depth D are decided to fall within the respective ranges of the referential values at Step S4, a scan is performed with the referential tube current mAb.

According to the present embodiment, the referential tube current mAb is corrected according to the width W and body depth D of the subject 5 to set a tube current in imaging mA without performing a scout scan separately from the scan performed at Step S7. The referential tube current mAb is defined taking account of a degree of X-ray absorption reflecting factors like the subject's width and body depth, and in addition, other factors; therefore, it is possible to set a suitable tube current mA without performing a scout scan to a degree of suitability comparable to a degree that would be otherwise achieved when the scout scan is performed. The elimination of the need for the scout scan enables improvement of the throughput and reduction of the exposure dose.

In the first embodiment, the emission condition setting section 76 may correct the referential tube current based on either one of the difference between the width W of the subject 5 and referential width Wb or the difference between the body depth D of the subject 5 and the referential body depth Db to set the tube current in imaging mA.

Next, a second embodiment will be described. The configuration of the X-ray CT system 1 in the second embodiment is identical to that in the first embodiment, and the operation is basically identical as well to that shown in the flow chart in FIG. 4. The second embodiment, however, is different from the first embodiment in the following points.

In the present embodiment, the referential emission condition is stored for each view angle of the X-ray tube 21. For example, referential emission conditions different from one another are stored for a plurality of required view angles. Here are stored a first referential emission condition for view angles of 0 and 180 degrees, and a second referential emission condition for view angles of 90 and 270 degrees. The first and second referential emission conditions are referential tube currents different from each other.

Figure 7:
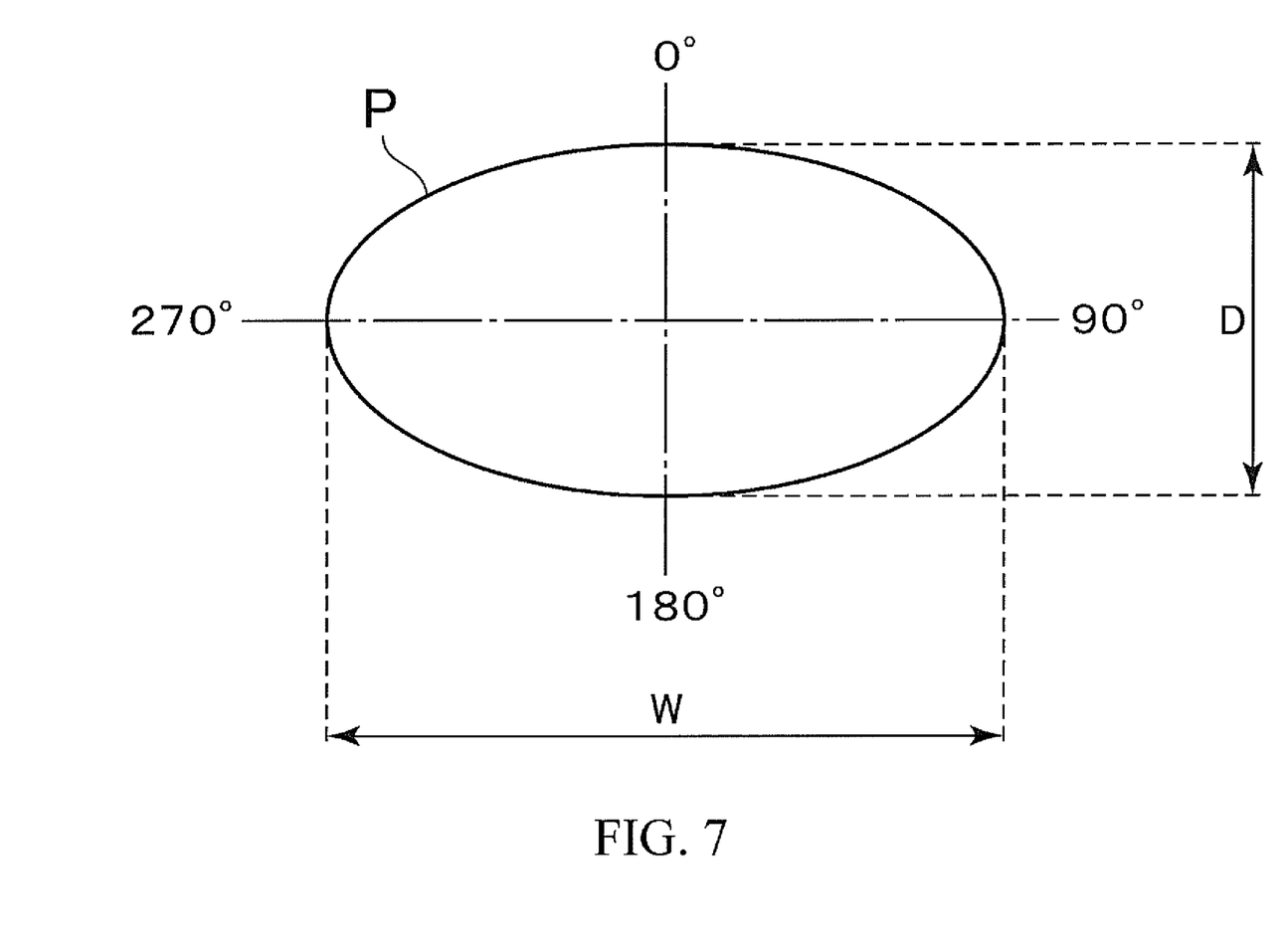
FIG. 7 A diagram explaining a relationship between the view angle and the subject's width and body depth.

Now assume that the referential tube current for view angles of 0 and 180 degrees is a first referential tube current, and that for view angles of 90 and 270 degrees is a second referential tube current. The first and second referential tube currents are stored for each body part of the subject. The subject P of standard body shape has some body parts where the dimension of the body depth D, which is the X-ray transmission path length for view angles of 0 and 180 degrees, is smaller than the dimension of the width W, which is the X-ray transmission path length for view angles of 90 and 270 degrees, as shown in FIG. 7. In this case, the first referential tube current is set to a value smaller than that of the second referential tube current.

At Step S5, the emission condition setting section 76 performs correction on the referential tube current using either one of a difference between the subject's width W identified by the width identifying section 74 and referential width Wb or a difference between the subject's body depth D identified by the body-depth identifying section 75 and the referential body depth Db according to the view angle of the X-ray tube 21. Specifically, the first referential tube current is corrected according to the difference between the subject's body depth D and referential body depth Db. The second referential tube current is corrected according to the subject's width W and referential width Wb. For example, the emission condition setting section 76 corrects the first referential tube current mAbf based on (EQ. 2) below to calculate a first tube current in imaging mAf, and corrects the second referential tube current mAbs based on (EQ. 3) below to calculate a second tube current in imaging mAs:

$$mAf=mAbf*F1 \qquad (EQ. 2)$$

where $F1=D/Db$, and $$mAs=mAbs*F2 \qquad (EQ. 3)$$

where $F2=W/Wb$.

As in the first embodiment, the first tube current mAf and second tube current mAs may be set for a plurality of body parts. In this case, the emission condition setting section 76 corrects the first referential tube current mAbf and second referential tube current mAbs for each of the plurality of body parts according to (EQ. 2) and (EQ. 3) above.

Figure 8:
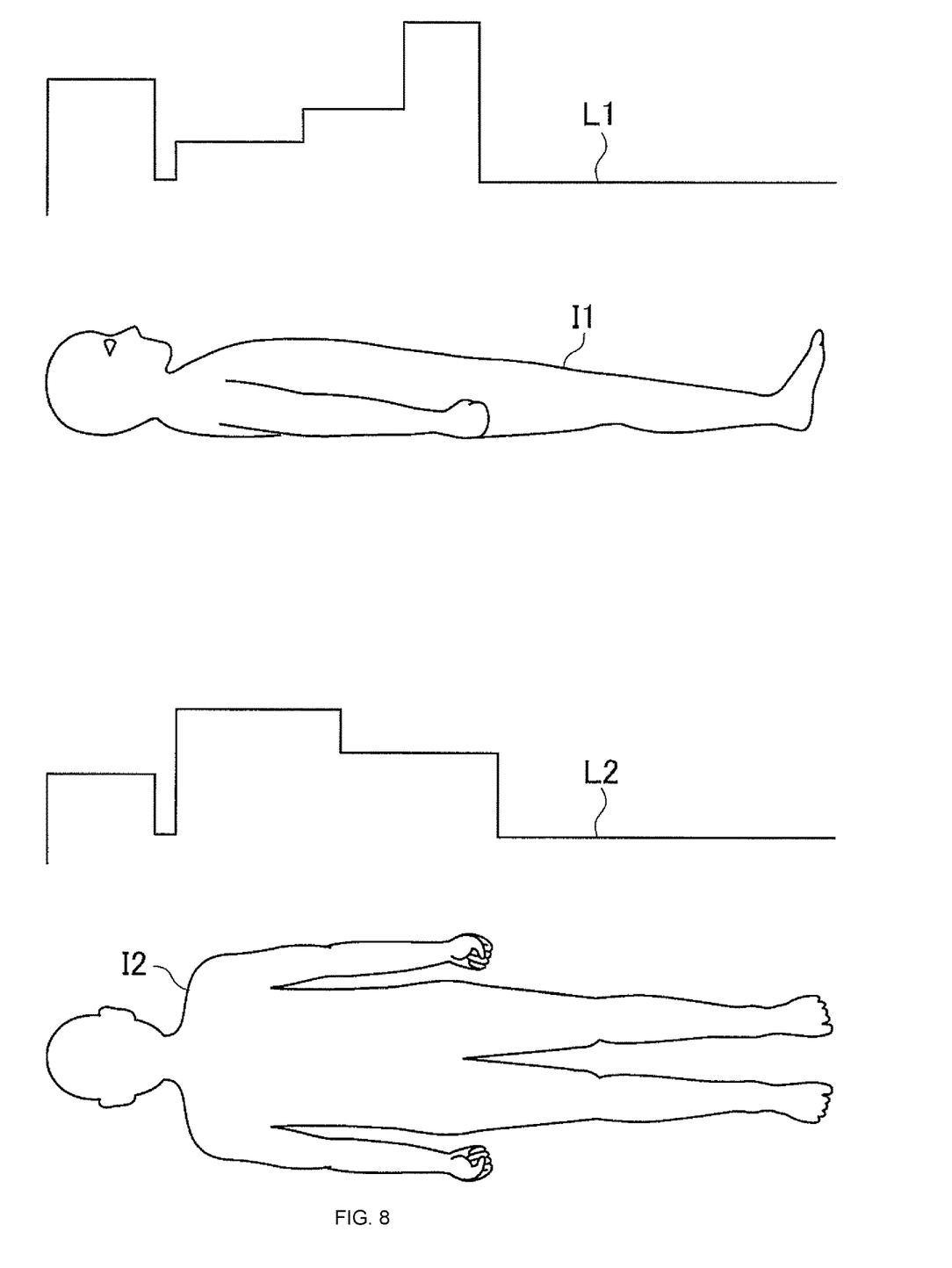
FIG. 8 A diagram showing a line chart representing a change of the tube current and a pictorial diagram representing the subject in a second embodiment.

At Step S6, the display control section 77 displays on the display device 62 a first line chart L1 representing a change of the first tube current mAf in the direction of the body axis of the subject 5 and a second line chart L2 representing a change of the second tube current mAs in the direction of the body axis of the subject 5, as shown in FIG. 8. The display control section 77 may also display a first pictorial diagram I1 and a second pictorial diagram 12 representing the subject along with the first line chart L1 and second line chart L2 on the display device 62. The first pictorial diagram I1 is a pictorial diagram of the subject as viewed in the x-axis direction so that the body depth is depicted, similarly to the pictorial diagram I in FIG. 6. The second pictorial diagram 12 is a pictorial diagram of the subject as viewed in the y-axis direction so that the width is depicted.

According to the present embodiment described above, a similar effect to that in the first embodiment may be obtained, and besides, a scan may be achieved with a tube current set more suitably according to the view angle.

Figure 9:
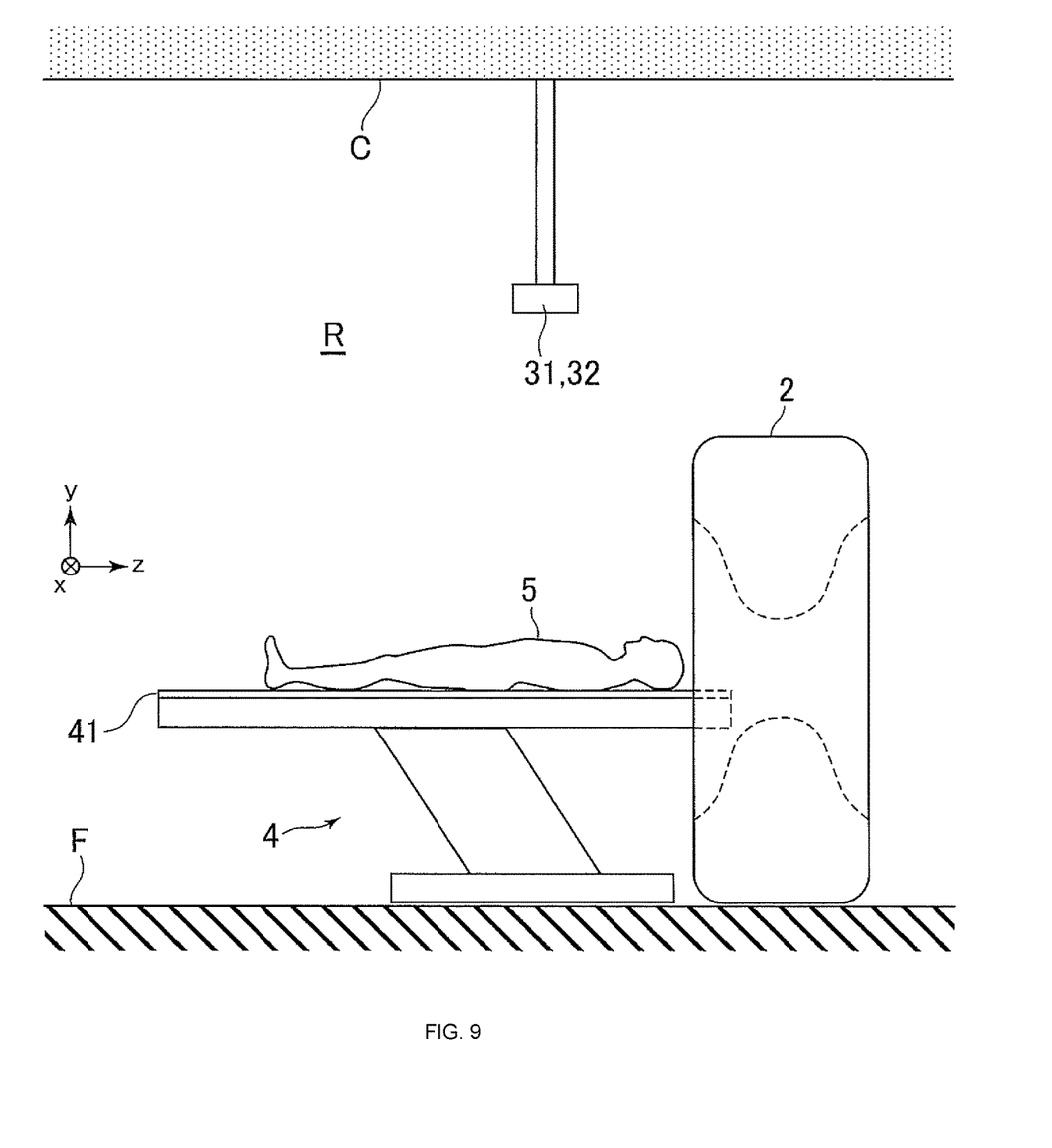
FIG. 9 A view showing another exemplary overview of the imaging room.

While the present invention has been described with reference to the embodiments, it will be easily recognized that the invention may be practiced with several modifications without changing the spirit and scope thereof. For example, the camera 31 and distance sensor 32 are not necessarily provided on the gantry 2. For example, the camera 31 and distance sensor 32 may be attached to the ceiling C of the examination room R, as shown in FIG. 9.

Moreover, the referential emission condition may be set assuming either one of the required referential width or required referential body depth for a subject. In this case, the emission condition setting section 76 corrects a referential emission condition based on either one of the difference between the width W of the subject 5 and referential width Wb or the difference between the body depth D of the subject 5 and referential body depth Db to set an emission condition in imaging.

Furthermore, the technique for identifying the width W and body depth D of the subject 5 is not limited to one that identifies them based on an image from the camera 31 and a detection signal from the infrared sensor 32.

The invention claimed is:

1. A radiation tomographic imaging system characterized in comprising:
   a radiation tube for emitting radiation onto a subject;
   a storage device for storing therein a referential emission condition for radiation emitted by said radiation tube, said referential emission condition being defined based on a required referential width, a required referential body depth in said subject and a degree of absorption of said radiation in said subject;
   an optical sensor for detecting a width and a body depth of said subject; and
   an emission condition setting section for setting an emission condition for radiation emitted by said radiation tube in imaging after correcting said referential emission condition according to at least one of a difference between the width of said subject detected by said optical sensor and said referential width, and a difference between the body depth of said subject detected by said optical sensor and said referential body depth.

2. The radiation tomographic imaging system as recited in claim 1, characterized in that: said referential emission condition is stored for each body part of a subject.

3. The radiation tomographic imaging system as recited in claim 1, characterized in that: said referential emission condition is stored for each view angle of said radiation tube.

4. The radiation tomographic imaging system as recited in claim 3, characterized in that: said emission condition setting section performs correction on said referential emission condition using either one of the difference between the width of said subject and said referential width or the difference between the body depth of said subject and said referential body depth according to the view angle of said radiation tube.

5. The radiation tomographic imaging system as recited in claim 1, characterized in that: said emission condition setting section corrects said referential emission condition so that a radiation dose increases as at least one of said width and said body depth is larger, and corrects said referential emission condition so that a radiation dose decreases as at least one of said width and said body depth is smaller.

6. The radiation tomographic imaging system as recited in claim 1, characterized in that: said optical sensor is an optical image capture apparatus and a distance sensor.

7. The radiation tomographic imaging system as recited in claim 1, characterized in comprising: a display device for displaying the radiation emission condition set by said emission condition setting section.

8. The radiation tomographic imaging system as recited in claim 1, wherein the referential emission condition includes a referential tube current and the emission condition includes a tube current for radiation emitted by said radiation tube.

9. The radiation tomographic imaging system as recited in claim 8, wherein correcting said referential emission condition comprises correcting the referential tube current (mAb) to calculate the radiation tube current (mA) according to the equation below:

$$mA = mAb * F$$

wherein $F = (W/Wb) * (D/Db)$ and wherein Wb is the referential width, Db is the referential body depth Db, W is the width of the said subject and D is the body depth of the said subject.

10. A radiation tomographic imaging system characterized in comprising:
   a radiation tube for emitting radiation onto a subject;
   a storage device for storing therein a referential emission condition for radiation emitted by said radiation tube, said referential emission condition being defined based on a required referential width, a required referential body depth in said subject and a degree of absorption of said radiation in said subject;
   an optical sensor for detecting a width and a body depth of said subject; and
   a processor, said imaging system being characterized in that:
      said processor executes by a program an emission condition setting function of setting an emission condition for radiation emitted by said radiation tube in imaging after correcting said referential emission condition according to at least one of a difference between the width of said subject detected by said optical sensor and said referential width, and a difference between the body depth of said subject detected by said optical sensor and said referential body depth.

11. A non-transitory storage medium comprising a computer program for controlling a radiation tomographic imaging system comprising:
   a radiation tube for emitting radiation onto a subject;
   a storage device for storing therein a referential emission condition for radiation emitted by said radiation tube, said referential emission condition being defined based on a required referential width, a required referential body depth in said subject and a degree of absorption of said radiation in said subject;

an optical sensor for detecting a width and a body depth of said subject; and a processor, said program being characterized in causing said processor to execute:

an emission condition setting function of setting an emission condition for radiation emitted by said radiation tube in imaging after correcting said referential emission condition according to at least one of a difference between the width of said subject detected by said optical sensor and said referential width, and a difference between the body depth of said subject detected by said optical sensor and said referential body depth.

* * * * *